United States Patent
Markman

(10) Patent No.: US 10,285,795 B2
(45) Date of Patent: May 14, 2019

(54) METHOD AND APPARATUS FOR CREATING A RECONSTRUCTIVE GRAFT

(71) Applicant: Barry Markman, Las Vegas, NV (US)

(72) Inventor: Barry Markman, Las Vegas, NV (US)

(73) Assignee: Markman Biologics Corporation, Las Vegas, NV (US)

( * ) Notice: Subject to any disclaimer, the term of this patent is extended or adjusted under 35 U.S.C. 154(b) by 124 days.

(21) Appl. No.: 15/487,585

(22) Filed: Apr. 14, 2017

(65) Prior Publication Data

US 2017/0216008 A1 Aug. 3, 2017

Related U.S. Application Data

(63) Continuation of application No. 14/678,188, filed on Apr. 3, 2015, now Pat. No. 9,622,845, which is a continuation-in-part of application No. 13/687,082, filed on Nov. 28, 2012, now Pat. No. 9,050,177, which is a continuation of application No. 13/101,022, filed on May 4, 2011, now Pat. No. 8,858,647.

(60) Provisional application No. 61/331,805, filed on May 5, 2010.

(51) Int. Cl.
*A61F 2/02* (2006.01)
*A61F 2/00* (2006.01)
*A61L 27/54* (2006.01)

(52) U.S. Cl.
CPC .......... *A61F 2/0077* (2013.01); *A61F 2/0063* (2013.01); *A61L 27/54* (2013.01); *A61F 2002/0068* (2013.01); *A61F 2002/0081* (2013.01); *A61F 2240/002* (2013.01); *A61F 2240/005* (2013.01); *A61F 2250/0026* (2013.01); *A61F 2250/0048* (2013.01); *A61F 2250/0051* (2013.01); *A61F 2250/0067* (2013.01)

(58) Field of Classification Search
CPC ........ A61F 2/02; A61F 2/0063; A61F 2/0077; A61F 2002/0081; A61F 2002/0068; A61F 2/00; A61F 2/105
See application file for complete search history.

(56) References Cited

U.S. PATENT DOCUMENTS

| | | |
|---|---|---|
| 4,950,296 A | 8/1990 | McIntyre |
| 5,728,159 A | 3/1998 | Stroever et al. |
| 5,759,205 A | 6/1998 | Valentini |
| 5,935,002 A | 8/1999 | Falgiclia |
| 5,971,849 A | 10/1999 | Falgiclia |
| 6,190,255 B1 | 2/2001 | Thomas et al. |

(Continued)

*Primary Examiner* — Vi X Nguyen
(74) *Attorney, Agent, or Firm* — Weide & Miller, Ltd.

(57) ABSTRACT

A method and apparatus is provided for creating an internal reconstruction tissue graft. Templates may be used to create a multitude of patterns in a variety of tissue reconstruction grafts. An apparatus may be used to create an internal tissue graft for reconstruction through either compression and/or removal of segments. An apparatus may be used, through either compression and or removal of segments of a pre-formed template made of synthetics and or metal that mirrors a template that can be used as an internal tissue graft for reconstruction. In a method, such as using software analysis and an apparatus, the physical properties of the tissue graft and its pre- and post-operative properties and appearance may be measured.

10 Claims, 3 Drawing Sheets

(56) References Cited

U.S. PATENT DOCUMENTS

| | | |
|---|---|---|
| 6,280,328 B1 | 8/2001 | Holch et al. |
| 6,911,220 B1 | 6/2005 | Sachs |
| 6,949,252 B2 | 9/2005 | Mizuno et al. |
| 7,066,962 B2 | 6/2006 | Swords |
| 7,189,259 B2 | 3/2007 | Simionescu et al. |
| 7,282,165 B2 | 10/2007 | Williams, III et al. |
| 7,416,546 B2 | 8/2008 | Pugsley et al. |
| 7,427,284 B2 | 9/2008 | Seedhom et al. |
| 7,458,975 B2 | 12/2008 | May et al. |
| 7,520,898 B2 | 4/2009 | Re et al. |
| 7,572,298 B2 | 8/2009 | Roller et al. |
| 7,645,568 B2 | 1/2010 | Stone |
| 7,723,108 B2 | 5/2010 | Truncale et al. |
| 7,727,278 B2 | 6/2010 | Olsen et al. |
| 7,776,089 B2 | 8/2010 | Bianchi et al. |
| 7,815,923 B2 | 10/2010 | Johnson et al. |
| 8,500,740 B2 | 8/2013 | Bojarski et al. |
| 8,597,687 B2 | 12/2013 | Daniel |
| 8,858,647 B2 | 10/2014 | Markman |
| 9,050,177 B2 | 6/2015 | Marman |
| 2004/0049270 A1* | 3/2004 | Gewirtz .................. A61F 2/28 623/17.11 |
| 2004/0082063 A1 | 4/2004 | Deshpande et al. |
| 2006/0219143 A1 | 10/2006 | Brennan et al. |
| 2007/0061015 A1 | 3/2007 | Jensen et al. |
| 2009/0291116 A1 | 11/2009 | Casellas |
| 2010/0119755 A1 | 5/2010 | Chung et al. |
| 2010/0137903 A1 | 6/2010 | Lee et al. |
| 2010/0161032 A1 | 6/2010 | Avellanet |
| 2011/0022171 A1 | 1/2011 | Richter et al. |
| 2015/0342725 A1 | 12/2015 | Cuevas et al. |

\* cited by examiner

METHOD AND APPARATUS FOR CREATING A RECONSTRUCTIVE GRAFT

RELATED APPLICATION DATA

This application is a continuation of U.S. application Ser. No. 14/678,188, filed Apr. 3, 2015, which is a continuation-in-part of U.S. application Ser. No. 13/687,082, filed Nov. 28, 2012, now U.S. Pat. No. 9,050,177, issued Jun. 9, 2015, which is a continuation of U.S. patent application Ser. No. 13/101,022, filed May 4, 2011, now U.S. Pat. No. 8,858,647, issued Oct. 14, 2014, and claims priority to U.S. Provisional Application Ser. No. 61/331,805, filed May 5, 2010, the contents of said earlier applications being incorporated by reference in their entirety herein.

FIELD OF THE INVENTION

The present invention relates to reconstructive tissue grafts.

BACKGROUND OF THE INVENTION

Current surgical reconstruction of internal tissue defects utilizes a solid, porous sheet with or without perforations. Current grafts allow for perforations that do enhance fluid egress and in growth of new tissue but due to the constrictive nature of such tissue grafts, the incidences of recurrences and the inability to expand with the application of increased pressure has allowed for a significant incidence of recurrence, stress tears, and an inability for expansion used in reconstructive and aesthetic procedures. Current tissue grafts also do not allow for the ability to enhance traction between the graft and specific anatomic points, similar in physical properties of how specific tread designs enhance traction between the tire and the road surface, as well as increase the time of utilization of the tire. The current novel invention applies these engineering applications to achieve similar results to internal surgical tissue grafts. None of the references below discuss the advantages of utilizing the current method and apparatus of applying designs and templates to internal surgical reconstructive grafts.

SUMMARY OF THE INVENTION

Figure 1A:
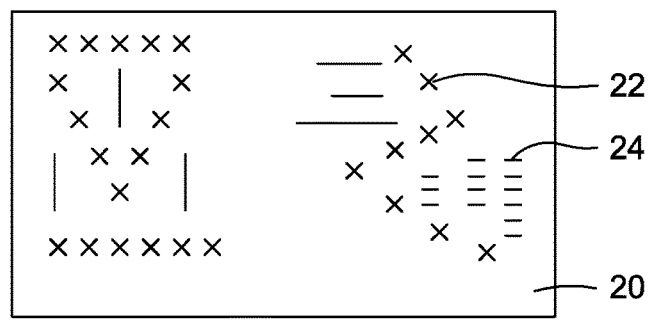
FIGS. 1A and 1B illustrate a top and bottom, respectively, of a tissue graft having patterns in accordance with the invention.

Various methods and apparatus for creating an internal reconstruction tissue graft are disclosed. Aspects of the invention comprise: 1) a method for the creation of templates used to create a multitude of patterns in a variety of tissue reconstruction grafts; 2) an apparatus that through either compression and or removal of segments of tissue create the internal tissue graft for reconstruction; 3) an apparatus that through either compression and or removal of segments of a preformed template (such as made of synthetics and or metal) that mirrors a template that can be used as an internal tissue graft for reconstruction; and/or 4) a method of measuring, through software analysis and an apparatus, the physical properties of the tissue graft and its pre and post-operative properties and appearance.

In one embodiment, a template is used to modify the surface of a tissue graft to include variable and multiple patterns, creating a modified or reconstructive graft which is configured for incorporation into a particular anatomic area.

In one embodiment, the invention is configured to, and an advantage of the invention comprises, reducing stress in grafts subject to continuous motion, such as, in the knee, hip, and cervical regions In one embodiment, the invention is configured to, and an advantage of the invention comprises, reducing stress in grafts subject to increased pressure gradients such as in the abdominal wall, inguinal hernia, and arterial grafts.

In one embodiment, the invention is configured to, and an advantage of the invention comprises, allowing for selective expandability (such as via partial or non-through expansion incisions and/or through expansion incisions of various thicknesses in the graft) in order to achieve better contour and external appearance.

In one embodiment, the invention is configured to, and an advantage of the invention comprises, allowing for selective expandability (such as via partial or non-through expansion incisions and/or through expansion incisions of various thicknesses in the graft) in order to achieve better outflow of blood in venous grafts.

In one embodiment, the invention is configured to, and an advantage of the invention comprises, allowing for selective traction or adhesion points of tissue grafts to key anatomic areas when needed in order to increase fixation at insertions and origins to reduce slippage of the graft.

In one embodiment, the invention is configured to, and an advantage of the invention comprises, promoting vascular in growth of the body's tissue in specific areas of the internal tissue graft.

In one embodiment, the invention is configured to, and an advantage of the invention comprises, allowing for an increase in the period of time of utilization and longevity of the internal reconstructive graft.

Another embodiment of the invention comprises methods and apparatus for creating a graft, such as a reconstructive tissue graft, which includes a medicant, such as antibiotics, growth factors, or chemotherapeutics, or other tissues, such as stem cells.

Further objects, features, and advantages of the present invention over the prior art will become apparent from the detailed description of the drawings which follows, when considered with the attached figures.

DETAILED DESCRIPTION OF THE INVENTION

Aspects of the invention comprise methods of making one or more templates which are usable to modify a tissue graft to create a modified tissue graft, such as by cutting or removing portions of the tissue graft or otherwise create surface patterns or other features; methods of modifying a tissue graft to create a modified reconstructive tissue graft, which reconstructive tissue graft may have features which are selected to address particular objectives relative to a particular anatomical site; and reconstructive grafts, including reconstructive tissue grafts which have features which are designed for particular medical goals and/or for a particular anatomical site.

One embodiment of the invention comprises a method of creating templates used to create a multitude of patterns in a variety of tissue reconstruction grafts. Such may consist of pre- or intra-operatively made templates.

In one embodiment, the templates may be based on an analysis of a particular anatomical region, such as software analysis of an image of initial tissue defect, the template designed to allow for a desired graft pattern to reduce the potential pressure, reduce stress, decrease wear and tear, provide traction, or achieve other objectives when implanted or placed at a particular anatomical site. Based on factors such as, but not limited to, the size, shape, thickness, width, variegations, type, and the desired surgical outcome, a tissue graft may be modified to include a pattern or other features. Due to the variability in a defect being reconstructed, such as the abdominal wall, breast, face, and extremities, different template patterns may be generated. Software analysis may be used to create an appropriate internal tissue graft for an identified existing defect.

In one embodiment, different materials may be used to make the templates and their respective patterns. In a preferred embodiment of the invention, internal reconstruction grafts may be created which not only permit mesh expansion, but provide for a multitude of various designs, shapes, patterns, variegations and materials to accommodate the existing defect to achieve the desired reconstructive and aesthetic results.

In one embodiment, software and/or hardware may be used to perform a pre-manufacture or pre-operative analysis. Templates may be constructed from a pre-made mold, and be made of different materials such as metal or plastic to be integrated with a compression device. The template can be integrated with a stationary or portable compression apparatus that can create prepackaged tissue grafts in a pre-manufactured configuration by a manufacturer or to be subsequently sterilized and used by a surgeon in the operating room. Alternatively, portable temples and/or compression devices can be used in a sterile operation room, or an apparatus may allow a surgeon or manufacturer to incise predetermined patterns into a tissue graft by a knife or other cutting implement. A primary objective of the invention allows for a tissue graft to be modified to create a reconstructive graft which is patterned to address or accommodate anticipated problems due to any and all activity and reconstructive and aesthetic results.

In one embodiment, an apparatus, either via compression and/or removal of segments of tissue, creates an internal tissue graft for reconstruction by creating a desired pattern within an internal tissue graft. Compression can be used against the template that in turn creates the desired internal pattern.

In a second methodology, pre-designed patterns of tissue mirror the specific designs on a pre-formed template that can be subsequently used on a portable compression and punch apparatus that can used to create the internal tissue graft in the operating room. Additional techniques using an apparatus that uses laser cutting technology can be utilized.

Figure 1B:
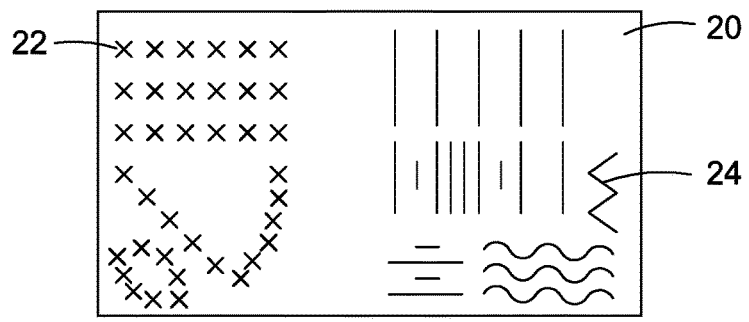
Figure 2:
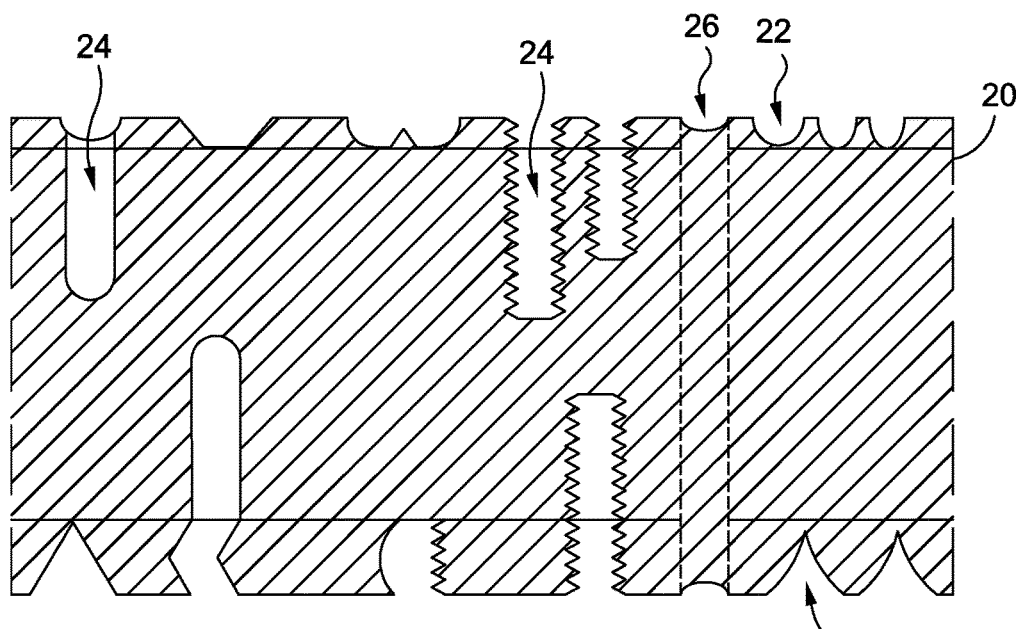
FIG. 2 is a side view of a tissue graft having various surface patterns in accordance with an embodiment of the invention, which patterns may be used to contain or retain medicants, tissues or other materials in accordance with other embodiments of the invention.

For example, FIG. 2 illustrates a tissue graft 20 where compression and/or removal of segments (such as spaced or separated by various distances between them) create recessed expansion patterns of various depths and shapes 22, adhesion projections of various heights and shapes 24 and through holes 26. FIGS. 1A and 1B illustrate one example of patterns of adhesion features 22 and expansion features 24 relative to a top (in FIG. 1A) and bottom (in FIG. 1B) of a tissue graft 20, which patterns may be used to generate a tissue graft having particular desired characteristics for a particular application.

Current medical devices are not applicable for creating the multitude of desired pattern grafts for each defect. In accordance with the invention, an apparatus can be used to create patterns applicable to a specific tissue defect, whether pre- or intra-operatively.

Measuring, such as through image capture and software analysis, the physical properties of the reconstructive tissue graft and its pre- and post-operative appearance may be utilized to correlate the physical properties of a created internal tissue graft and desired reconstructive and aesthetic grafts.

Broadly the present invention is directed to methods, apparatus, and devices involving variable templates for the purpose of internal reconstruction of body tissues including, but not limited to, a breast, the abdominal wall, vascular, and extremities. In a first method in accordance with the present invention, a template is created that allows for increased flexibility as it relates to the graft, and subsequently the need to contouring to sling a breast implant used in achieving a natural result for the patient. The template is pre-made or created during the reconstruction procedure to enhance the physical properties of the internal tissue graft to meet the requirements of the tissue grafts expectations, whether it is enhanced expansion, flexibility, traction, or period of utilization in anatomic areas where it is placed.

In one embodiment of the invention, the tissue reconstructive grafts are composed of cadaveric human tissue. In other embodiments, the tissue reconstructive grafts may be composed of cellular non-human tissue, including cellular and acellular processed graft. The tissue reconstructive grafts may also be composed of synthetic materials.

The features of the reconstructive tissue grafts, such as created using the templates may vary: (1) the designated patterns may vary by the distance between them and the patterns can be of various shapes, widths, thicknesses, and variegations; the designated patterns or other features can be either full thickness or partial thickness of the graft; the designated patterns can be on both anterior and posterior surfaces of the graft; the designated patterns may be configured to provide enhanced controlled expansion of the tissue graft; the designated patterns may be configured to provide enhanced stress relief during motion of the tissue graft; the designated patterns may be configured to provide enhanced adhesion between the tissue graft and anatomic region; the designated patterns may be configured to provide enhanced retention of various medicants and materials both in vitro and in vivo; the designated patterns may be configured to provide enhanced longevity and utilization of the graft.

Templates or other apparatus which are used to modify a tissue graft to create a modified reconstructive tissue graft may be made of a variety of materials, including synthetics, plastic, and metals; the templates or other apparatus may be used in a manufacturing facility or operating room; the templates or other apparatus may be operable by manual pressure, air pressure, hydraulic pressure, or electrically driven apparatus such as motor driven presses or screws, including via a portable compression device.

As indicated herein, the reconstructive graft may include various surface or other features, including for enhancing the retention of medicants or other materials (unless otherwise indicated, the term "medicants" as used herein may include medicants, tissues or other materials, as described below). In one embodiment, for example, surface features such as projections, channels, depressions, voids, pockets or the like may be formed in or through the tissue graft for accepting one or more medicants (including but not limited to chemotherapeutics, antibiotics, growth factors or other drugs), other tissues (including human non-human tissue, synthetic tissue, stems cells or the like) or other materials such as rebar (or other supportive or strengthening materials). In one embodiment, the reconstructive tissue graft may be pre-created with such features and then the medicants, other tissues or materials may be associated with the reconstructive tissue graft at a later time, such as before or during surgery. In other embodiments, a reconstructive tissue graft may have such materials pre-associated. For example, a tissue graft may be modified by forming one or more pockets, sleeves, folds, voids or the like, and one or more medicants, tissues or other materials may be associated with those pockets or voids during manufacture. The pre-configured, pre-medicated reconstructive tissue graft may then be provided to the surgeon for use. It will be appreciated that while medicants may be associated with a reconstructive tissue graft, other materials might also be associated, such as other types of tissue (as described above), bone material, or even metal meshes, or a variety of other materials (such as depending upon the particular anatomical region and/or condition for which the reconstructive tissue graft is intended).

The templates of the invention and/or other apparatus may be used to place such medicants or other materials. For example, one template may be used to modify the tissue graft, such as by creating the surface patterns, while other apparatus or devices may be used to associate the medicants or other materials (such as a medicant implanter, etc). In other embodiments, these functions may be combined (such as by having the template modify the graft and place the medicants or other materials or facilitate their placement by associated apparatus).

Figure 3A:
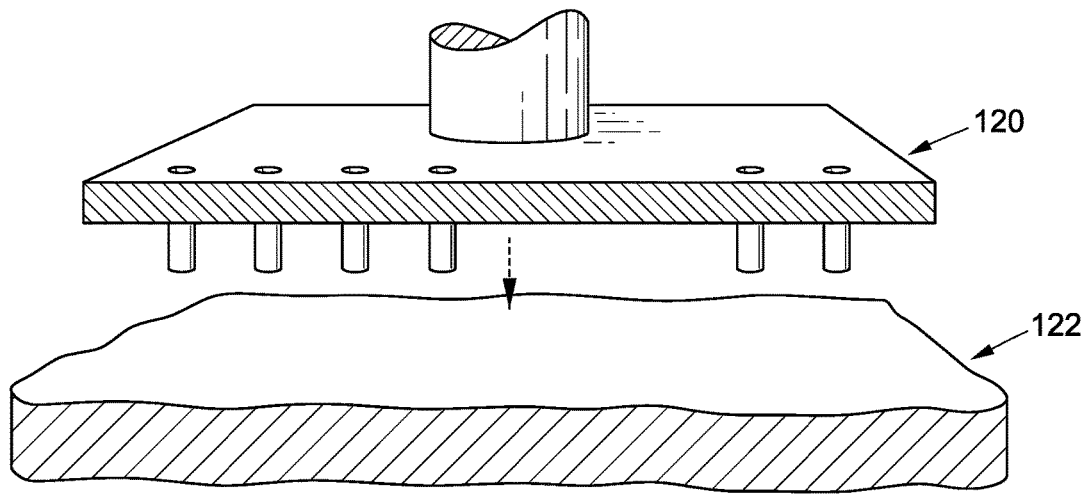
FIGS. 3A, 3B, and 3C illustrate a method of modifying a tissue graft with a template to create a modified tissue graft having one or more surface patterns and associating one or more medicants with said surface patterns in accordance with an embodiment of the invention.
Figure 3B:
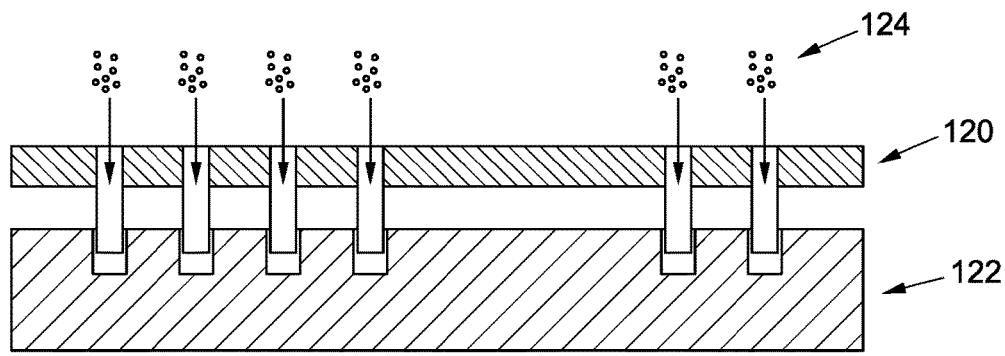
Figure 3C:
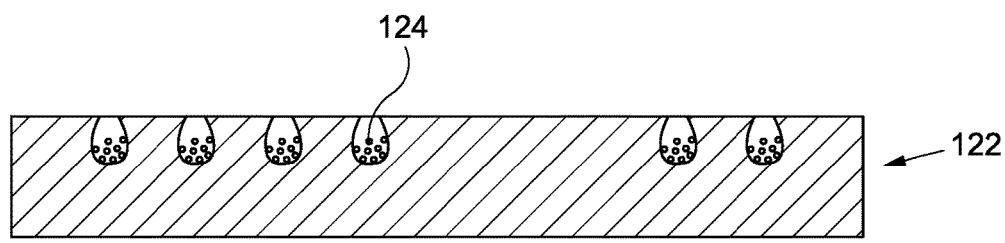

For example, FIG. 3A illustrates use of a template 120 to modify a tissue graft 122, such as by using the template 120 to cut or remove portions of a surface of the graft 122. As illustrated in FIG. 3B, the template 120 or another device may be used to associate a medicant 124 (or other material such as tissue, as described above) with one or more of the created surface features. FIG. 3C illustrates one embodiment of a modified graft 122 which includes one or more surface features and an associated medicant 124. This pre-prepared modified graft 122 may then be located in a particular anatomical area of a patient.

Figure 3D:
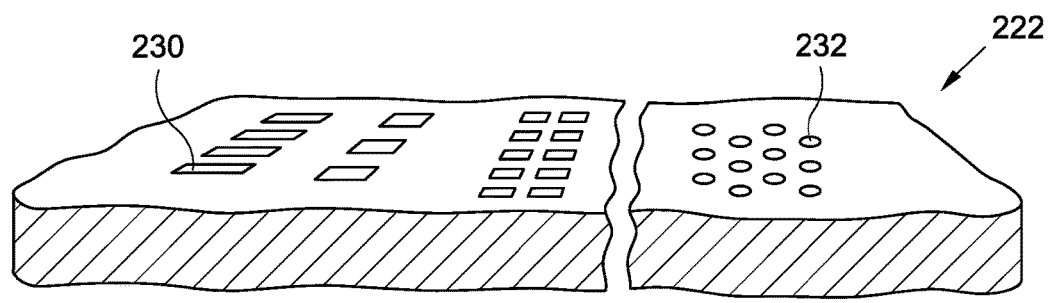
FIGS. 3D and 3E illustrate additional embodiments of a modified tissue graft in accordance with the invention.

FIG. 3D illustrates another embodiment of a modified graft 222 in accordance with the invention. As illustrated, the modified graft 222 may include one or more surface modifications, such as slots 230 which facilitate controlled expansion of the modified graft, such as described above. The modified graft 222 might, in addition or alternatively, include one or more features 232 which retain medicants. In one embodiment, the medicant retaining features are configured to evenly/spacially distribute the associated medicants. As illustrated, this may be accomplished by evenly distributed medicant retaining features. However, as one aspect of the invention, the medicant retaining features may have varying sizes or locations which are configured to cause associated medicants to be distributed in other controlled fashions (such as accounting for factors such as the configuration of the modified tissue graft, including varying thickness thereof, and anatomical features where the graft is to be placed, such as higher or lower blood flow in regions adjacent to the graft when implanted).

Figure 3E:
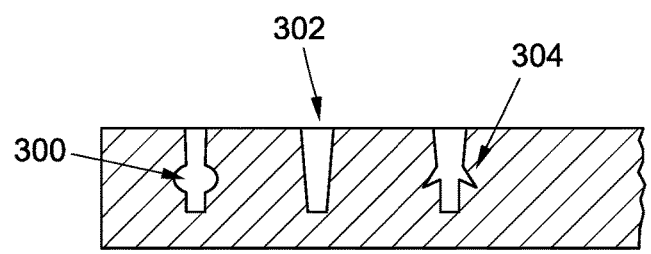

As illustrated in FIG. 2, modification of the tissue graft 20 to include one or more surface features results in a modified tissue graft which has a greater effective surface area than the original unmodified graft. In particular, as illustrated in FIG. 2, the created recesses, holes and the like have a surface area which is greater than the original unaltered surface area of the graft 20, thus causing the modified tissue graft to have an increased surface area which allows a greater amount of medicant or other secondary material to be associated therewith, as described herein. Aside from this, other features may have other or additional benefits. For example, FIG. 3E illustrates different medicant retaining features. As one example, a medicant retaining feature may comprise or include a void, such as a bulbous cavity 300 formed in the tissue graft. As another example, the feature might comprise a void or cavity which includes a valve 302. The valve 302 may be used to retain the medicants in the graft during placement and/or control the flow or release of medicant or other materials from the associated cavity to the exterior of the graft). The valve 302 might, for example, be formed of a portion of the tissue graft itself, such as an upper layer of the tissue graft which is perforated or slit. As yet another example, the feature might comprise a punch-type feature 304 which includes one or more voids, cavities, pockets or the like which can be used to retain medicants. Of course, as indicated herein, the size and shape of the medicant retaining features may vary.

In one embodiment, the medicant retaining feature is intended to retain one or more medicants (or other materials, as described herein) for release once the tissue graft is located at the desired anatomical site. In other embodiments, the retaining feature might retain the medicant or other material once the graft is placed. For example, a synthetic mesh material which is located in the graft may remain in the graft after it is placed, thus strengthening the graft and/or the integration of the graft with the anatomical site.

The above description represents one embodiment of the present invention. However, many variations to the method and apparatus are possible without deviating from the scope of the invention. It will be understood that the above described arrangements of apparatus and the method described herein are merely illustrative of applications of the principles of this invention and many other embodiments and modifications may be made without departing from the spirit and scope of the invention as defined in the claims.

What is claimed is:

1. A reconstructive tissue graft for placement at an anatomical site of a human, said reconstructive tissue graft prepared by a process comprising the steps of:
   modifying an exterior surface of a tissue graft obtained from a site other than said anatomical site to include one or more designed surface features, said designed surface features comprising one or more openings; and
   associating at least one medicant, secondary tissue or other material with one or more of said designed surface features comprising at least partially filling said one or more openings.

2. The reconstructive tissue graft in accordance with claim 1 wherein said tissue graft comprises human tissue.

3. The reconstructive tissue graft in accordance with claim 2 wherein said human tissue comprises soft, non-bone, tissue.

4. The reconstructive tissue graft in accordance with claim 1 wherein said at least one medicant comprises one or more of an antibiotic, a hormone, a growth factor and a chemotherapeutic agent.

5. The reconstructive tissue graft in accordance with claim 1 wherein said other material comprises one or more of acellular human tissue, non-human tissue, stem cells and at least one synthetic material.

6. The reconstructive tissue graft in accordance with claim 1 wherein said one or more designed surface features comprise one or more voids, pockets, sleeves, channels, depressions, projections and folds at said exterior surface of said tissue graft.

7. The reconstructive tissue graft in accordance with claim 1 wherein said step of modifying comprises removing material from one or more areas of said exterior surface of said tissue graft.

8. The reconstructive tissue graft in accordance with claim 7 wherein said step of removing comprises or more of cutting and punching.

9. A reconstructive tissue graft for placement at an anatomical site of a human, said reconstructive tissue graft prepared by a process comprising the steps of:
   modifying an exterior surface of a tissue graft having a first surface area, said tissue graft obtained from a site other than said anatomical site to include one or more designed surface features, said designed surface features causing said tissue graft to have a second increased surface area which is greater than said first surface area, one or more of said designed surface features comprising pockets created by punching material from said tissue graft; and
   associating at least one medicant, secondary tissue or other material with at least a portion of said exterior surface of said tissue graft which includes one or more of said designed surface features.

10. The reconstructive tissue graft in accordance with claim 9 wherein said one or more designed surface feature comprise one or more pockets extending into said exterior surface of said tissue graft.

* * * * *